United States Patent
Gaither et al.

(10) Patent No.: US 11,459,678 B2
(45) Date of Patent: *Oct. 4, 2022

(54) KNIT SOCK WITH TARGETED COMPRESSION ZONES, AND METHOD FOR LIFTING AND STRETCHING THE PLANTAR FASCIA

(71) Applicant: Flagship Brands, LLC, Hickory, NC (US)

(72) Inventors: Hugh Gaither, Charlotte, NC (US); John Gaither, Charlotte, NC (US); James Richard, Newton, NC (US)

(73) Assignee: Flagship Brands, LLC, Hickory, NC (US)

( * ) Notice: Subject to any disclaimer, the term of this patent is extended or adjusted under 35 U.S.C. 154(b) by 202 days.

This patent is subject to a terminal disclaimer.

(21) Appl. No.: 17/013,011

(22) Filed: Sep. 4, 2020

(65) Prior Publication Data

US 2020/0399800 A1    Dec. 24, 2020

Related U.S. Application Data

(63) Continuation of application No. 15/804,606, filed on Nov. 6, 2017, now Pat. No. 10,767,289, which is a
(Continued)

(51) Int. Cl.
*D04B 1/26* (2006.01)
*D04B 1/10* (2006.01)

(52) U.S. Cl.
CPC .............. *D04B 1/26* (2013.01); *D04B 1/102* (2013.01); *D04B 1/265* (2013.01); *D10B 2403/02* (2013.01)

(58) Field of Classification Search
CPC . D04B 1/26; D04B 1/265; D04B 9/52; D04B 9/56; A41B 11/003
See application file for complete search history.

(56) References Cited

U.S. PATENT DOCUMENTS 2,100,861 A    11/1937    Lochhead
2,102,368 A    12/1937    Martel
(Continued)

FOREIGN PATENT DOCUMENTS

WO    WO-2007091304    8/2007

OTHER PUBLICATIONS

U.S. Appl. No. 15/716,953, filed Sep. 2017, Gaither.

*Primary Examiner* — Danny Worrell
(74) *Attorney, Agent, or Firm* — Schwartz Law Firm, P.C.

(57) ABSTRACT

A knit sock is integrally formed of a body yarn in circumferential courses and axial wales, and includes a foot portion having a heel and a toe, and an ankle portion joined to the foot portion and defining an open leg end of the sock. A first targeted compression zone is formed with the foot portion between the heel and the toe, and includes spaced-apart axial compression ridges extending axially outward from the heel at a first end of the first compression zone to a second end of the first compression zone. A second targeted compression zone is formed with the ankle portion between the heel and the open leg end of the sock, and includes spaced-apart axial compression ridges extending axially outward from the heel at a first end of the second compression zone to a second end of the second compression zone.

20 Claims, 14 Drawing Sheets

Related U.S. Application Data continuation-in-part of application No. 15/716,953, filed on Sep. 27, 2017, now Pat. No. 10,011,926.

(60) Provisional application No. 62/448,652, filed on Jan. 20, 2017.

(56) References Cited

U.S. PATENT DOCUMENTS

| | | |
|---|---|---|
| 2,219,235 A | 10/1940 | Morton |
| 2,379,649 A | 7/1945 | Nebel |
| 3,154,933 A | 11/1964 | Holder |
| 3,157,037 A | 11/1964 | Nebel et al. |
| 3,162,029 A | 12/1964 | Laws et al. |
| 4,015,448 A | 7/1977 | Knohl |
| 4,034,581 A | 7/1977 | Swafford |
| 4,194,249 A | 3/1980 | Thorneburg |
| 4,216,662 A | 8/1980 | Harris, Jr. et al. |
| 4,253,317 A | 3/1981 | Howard et al. |
| 4,255,949 A | 3/1981 | Thorneburg |
| 4,277,959 A | 7/1981 | Thorneburg |
| 4,494,388 A | 1/1985 | Lau et al. |
| 4,522,044 A | 7/1985 | Lineberry et al. |
| 4,589,267 A | 5/1986 | Barbee |
| 4,732,015 A | 3/1988 | Abrams et al. |
| 5,115,650 A | 5/1992 | Patrick et al. |
| 5,184,485 A | 2/1993 | Bini |
| 5,983,402 A | 11/1999 | Fincher |
| 6,092,397 A | 7/2000 | Cortinovis |
| 6,336,227 B1 | 1/2002 | Liput |
| 6,505,485 B1 | 1/2003 | Eiseberg |
| 6,805,681 B2 | 10/2004 | Yokoyama |
| 7,721,575 B2 | 5/2010 | Yokoyama |
| 7,757,518 B2 | 7/2010 | Sho et al. |
| 7,950,071 B2 | 5/2011 | Jeong |
| 7,971,280 B2 | 7/2011 | Kaneda |
| D657,122 S | 4/2012 | Gaither |
| D657,123 S | 4/2012 | Gaither |
| 8,424,116 B2 | 4/2013 | Anastsopoulos et al. |
| 8,495,765 B2 | 7/2013 | Araki et al. |
| 8,973,411 B2 | 3/2015 | Gaither |
| D752,334 S | 3/2016 | Easter |
| 9,803,300 B2 | 10/2017 | Gaither |
| 2006/0085894 A1 | 4/2006 | Yakopson et al. |
| 2006/0247566 A1 | 11/2006 | Bet |
| 2007/0113593 A1 | 5/2007 | Jeong |
| 2008/0249454 A1 | 10/2008 | Mills |
| 2009/0158404 A1 | 6/2009 | Hahn et al. |
| 2013/0263629 A1 | 10/2013 | Gaither |

KNIT SOCK WITH TARGETED COMPRESSION ZONES, AND METHOD FOR LIFTING AND STRETCHING THE PLANTAR FASCIA

TECHNICAL FIELD AND BACKGROUND OF THE INVENTION

This invention relates generally to knit hosiery, and more particularly to a circularly-knit sock with a targeted compression zones designed to lift and stretch the plantar fascia of the foot. In various exemplary applications, the targeted compression zones of the present sock may also function alone or in combination with other features to "lock" the sock in position on the foot of the wearer during use. In addition to improved fit and comfort, the present sock may enhance a runner's proprioception, kinesthetic awareness, stamina or endurance, and overall performance.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises a knit sock including a foot portion having an upper instep area and a lower sole area integrally knit of a body yarn in circumferential courses and axial wales. The lower sole area defines inner and outer arch regions. The inner arch region comprises a targeted (predefined) compression zone adapted to reside generally adjacent an inner arch of a wearer's foot. The compression zone comprises axially extending compression ridges of variable length spaced apart from a top of the compression zone to a bottom of the compression zone. When the sock is worn, a compression force applied by the foot portion within the targeted compression zone is greater than the compression force in directly adjacent areas of the foot portion.

The term "targeted compression zone" as used herein refers to a predefined area of the sock which is of greater density than directly adjacent areas, and which is fabricated to apply greater compression force against an arch of the foot.

In this context of the present disclosure, the term "directly adjacent" means a fabric area located or formed beside or surrounded (in whole or in part) by another fabric area without intervening fabric, parts or other structure.

The term "sock" refers broadly herein to any hosiery or other fabric construction designed to cover at least a portion of the wear's foot or other body part. The sock may be knit in whole or in part (e.g., using conventional circular knitting machinery), and may be specially designed for a variety of uses including running, cycling, hiking, golf, hunting, and other general athletic and every-day wear. The sock may comprise a footsock, tube sock, calf-high sock, mid-calf or over-the calf sock, crew sock, stocking, stretch or support hosiery, foot sleeve, foot wrap, or the like. The present sock may also be integrally formed with other garments, such as pantyhose. In further alternative embodiments, the exemplary "sock" may have opposing open ends, and may comprise or be incorporated in other garments such as arm sleeves, calf sleeves, thigh sleeves, and the like.

According to another exemplary embodiment, the targeted compression zone comprises elastic yarns laid-in the body yarn. Alternatively, the compression zone may be separately formed and separately attached (e.g., by sewing) to parts of the sock.

According to another exemplary embodiment, the targeted compression zone is generally semi-circular. The term "semi-circular" is defined broadly herein to mean any shape having a first side which is generally linear and a second side which is generally arcuate. The compression zone may also be formed in a variety of other shapes including, for example, oval, circular, pyramidal, square, and rectangular.

According to another exemplary embodiment, the targeted compression zone comprises a substantially arcuate side extending between opposite ends of the foot portion, and a substantially linear side opposite the arcuate side.

According to another exemplary embodiment, the arcuate side of the compression zone faces a bottom axial centerline of the foot portion (substantially dividing the lower sole area into inside and outside arch regions).

According to another exemplary embodiment, the linear side of the compression zone extends proximate an inside axial centerline of the foot portion (substantially dividing the lower sole area and the upper instep area).

According to another exemplary embodiment, the compression zone comprises a plurality of spaced axial compression ridges. Each compression ridge may be formed by one or more uncut pattern (or accent or other) yarns. The term "uncut" refers to a single length of yarn extending coursewise across each of the axial wales in the compression zone. In other words, a first free end of the uncut yarn may reside outside a first wale of the compression zone, while the opposite free end resides outside the last wale of the compression zone. These uncut yarns may be thicker than the body yarn, and may be integrated into the compression zone in each circumferential course.

According to another exemplary embodiment, the compression ridges taper (become shorter) in axial length from the linear side of the compression zone towards a center of the arcuate side of the compression zone.

According to another exemplary embodiment, the compression zone comprises double covered elastic yarns.

According to another exemplary embodiment, the size of each double covered elastic yarn is less than 250 denier. In one specific embodiment, the denier range is 90 to 580.

According to another exemplary embodiment, the compression zone has a tighter gauge (or increased stitch density) than directly adjacent areas of the foot portion. The density in the compression zone may be 50%-100% greater than the density in directly adjacent areas of the sock. In one example, the density in the compression zone is about 70% greater than the density in directly adjacent areas of the sock.

According to another exemplary embodiment, the compression zone has a knit structure distinct from directly adjacent areas of the foot portion.

According to another exemplary embodiment, the foot portion further comprises a heel and a toe.

According to another exemplary embodiment, the upper instep area of the foot portion comprises an intermediate flat knit region.

According to another exemplary embodiment, the intermediate flat knit region in the upper instep area comprises mock ribbing.

According to another exemplary embodiment, the upper instep area of the foot portion further comprises first and second mesh knit regions directly adjacent or adjacent (i.e, proximate) opposite sides of the intermediate flat knit region.

According to another exemplary embodiment, the outer arch region of the lower sole area comprises mock ribbing.

In yet another exemplary embodiment, the present disclosure comprises a knit sock with a foot portion having an upper instep area and a lower sole area integrally knit of a body yarn in circumferential courses and axial wales. The lower sole area comprises a generally semi-circular targeted compression zone. A compression force applied by the foot portion within the targeted compression zone is greater than the compression force in directly adjacent areas of the foot portion.

According to another exemplary embodiment, the targeted compression zone has reduced coursewise and walewise stretchability relative to directly adjacent areas of the foot portion.

In yet another exemplary embodiment, the present disclosure comprises a knit sock integrally formed of a body yarn in circumferential courses and axial wales, and comprising a foot portion having a heel and a toe (open or closed), and an ankle portion joined to the foot portion and defining an open leg end of the sock. A first targeted compression zone is formed with the foot portion between the heel and the toe, and comprises spaced-apart axial compression ridges extending axially outward from the heel at a first end of the first compression zone to a second end of the first compression zone. Adjacent axial compression ridges have different termination points at the second end of the first compression zone. A second targeted compression zone is formed with the ankle portion between the heel and the open leg end of the sock, and comprises spaced-apart axial compression ridges extending axially outward from the heel at a first end of the second compression zone to a second end of the second compression zone. Adjacent axial compression ridges have different termination points at the second end of the second compression zone. A compression force applied by the sock (to the foot of the wearer) within the first and second targeted compression zones is greater than the compression force in directly adjacent areas of the sock.

According to one exemplary embodiment, each of the compression ridges may be formed by one or more uncut pattern (or accent or other) yarns. As previously described, the term "uncut" refers to a single length of yarn extending coursewise across each of the axial wales in the compression zone. In other words, a first free end of the uncut yarn may reside outside a first wale of the compression zone, while the opposite free end resides outside the last wale of the compression zone. These uncut yarns may be thicker than the body yarn, and may be integrated into the compression zone in each circumferential course.

According to another exemplary embodiment, the first and second targeted compression zones comprise elastic yarns laid-in the body yarn.

According to another exemplary embodiment, the first targeted compression zone is centrally pointed at its second end, and is adapted to extend under the foot generally from a lateral malleolus to a medial malleolus of the wearer.

According to another exemplary embodiment, the second targeted compression zone is centrally pointed at its second end, and is adapted to extend around a back of the heel generally from a lateral malleolus to a medial malleolus of the wearer.

According to another exemplary embodiment, the heel of the foot portion comprises a heel pocket defined by upper and lower reciprocation lines. The first end of the first targeted compression zone is formed at the lower reciprocation line of the heel pocket, and extends axially from the heel pocket in a direction towards the toe of the foot portion.

According to another exemplary embodiment, the heel of the foot portion comprises a heel pocket defined by upper and lower reciprocation lines. The first end of the second targeted compression zone is formed at the upper reciprocation line of the heel pocket, and extends axially from the heel pocket in a direction towards the open leg end of the sock.

According to another exemplary embodiment, the first and second targeted compression zones comprise double covered elastic yarns.

According to another exemplary embodiment, the first and second targeted compression zones have an increased density as compared to directly adjacent areas of the sock.

According to another exemplary embodiment, the first and second targeted compression zones have a knit structure distinct from directly adjacent areas of the sock.

In yet another exemplary embodiment, the present disclosure comprises a knit sock integrally formed of a body yarn in circumferential courses and axial wales. The sock has a foot portion with a heel and a toe (open or closed), and an ankle portion joined to the foot portion and defining an open leg end of the sock. A targeted compression zone is formed with the ankle portion between the heel and the open leg end, and comprises spaced-apart axial compression ridges. The compression ridges extend axially outward from the heel at a first end of the targeted compression zone to a second end of the targeted compression zone. Adjacent axial compression ridges have different termination points at the second end of the targeted compression zone. A compression force applied by the sock (to the foot of the wearer) within the targeted compression zone is greater than the compression force in directly adjacent areas of the sock.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
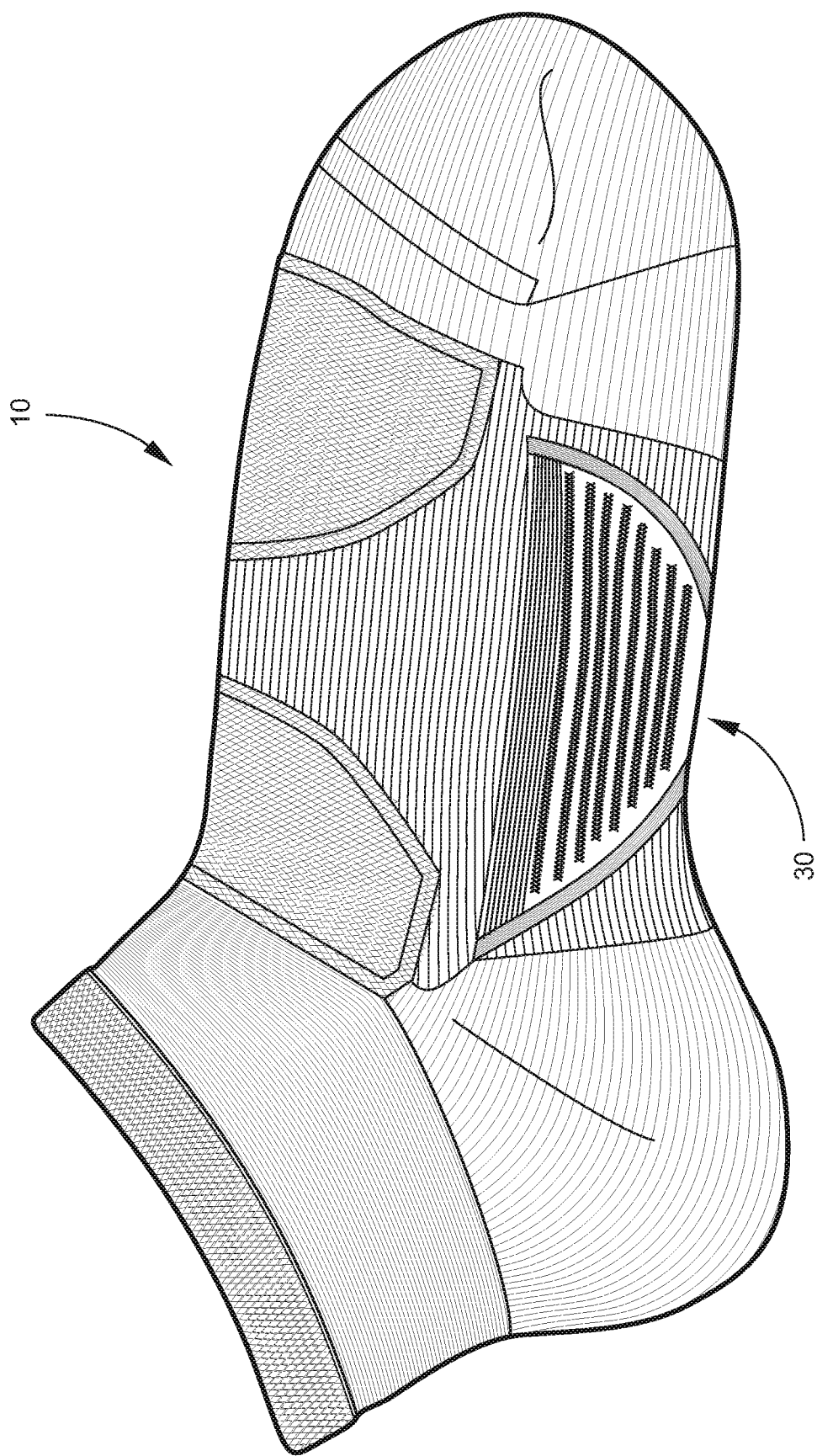
FIG. 1 is a side view of a knit sock incorporating a targeted compression zone according to one exemplary embodiment of the present disclosure.
Figure 2:
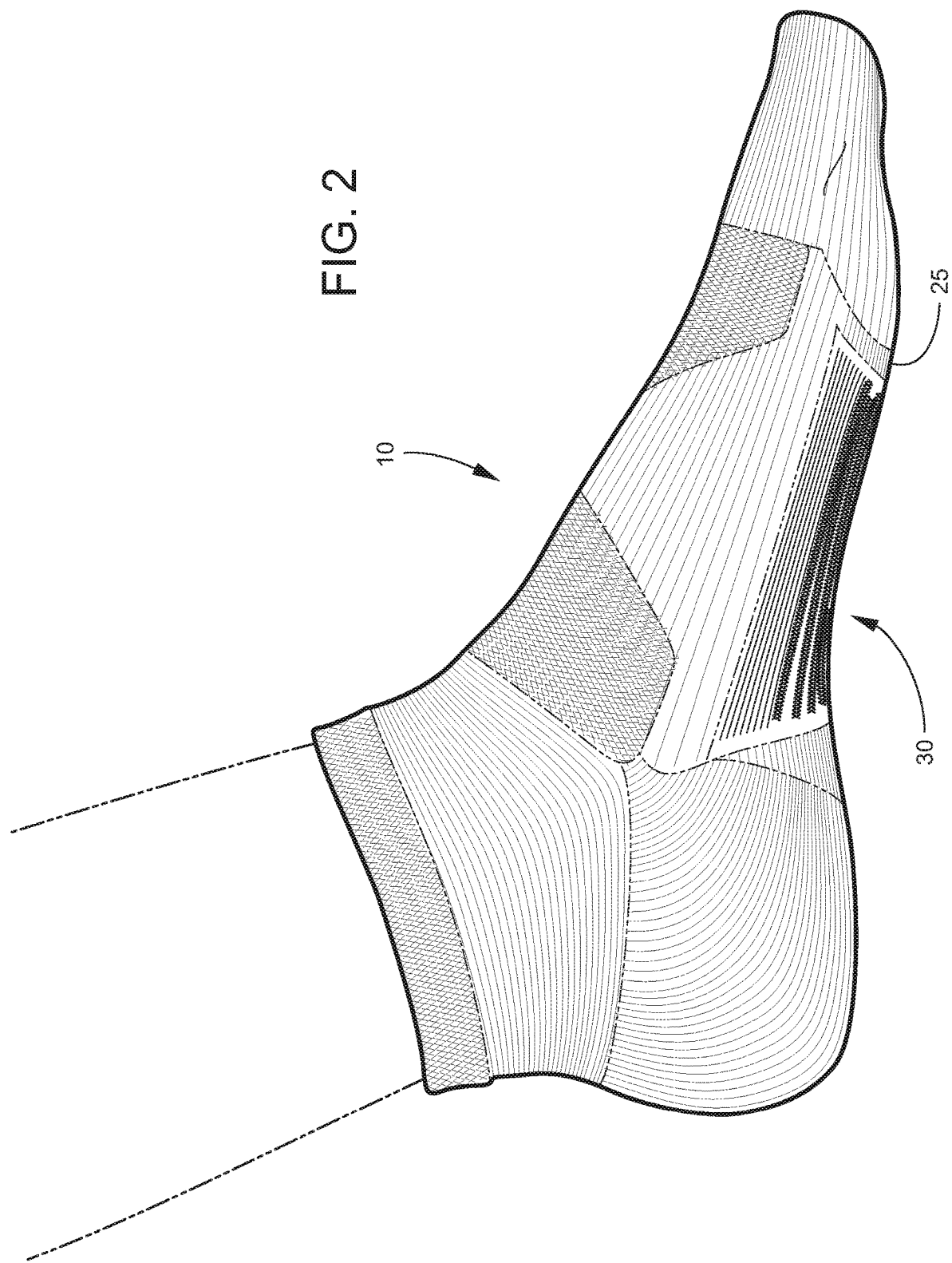
FIG. 2 is a side view of the exemplary sock worn on a foot of wearer, and including surface shading to indicate various areas and regions of distinct knit structure.

Referring now specifically to the drawings, a knit sock according to one exemplary embodiment of the present disclosure is illustrated in FIGS. 1 and 2, and shown generally at reference numeral 10. The exemplary sock 10 is constructed on a circular hosiery knitting machine, and includes a plurality of yarns formed in needle and sinker loops extending in circumferential courses and axial wales. The sock 10 may be formed throughout of a body yarn and a ground yarn knitted in plated relationship in various stitch constructions described below, and with inlaid elastic yarns and pattern yarns in certain portions, areas, and regions of the sock.

Referring to FIGS. 3-6, the exemplary sock 10 comprises an integrally-knit raised ankle portion 11 and foot portion 12. The foot portion 12 includes an upper instep area 14, a lower sole area 15, and a reciprocally-knitted heel 16 and toe 17. The upper instep area 14 and lower sole area 15 are circularly-knit in foot portion 12 and designated by notional center lines ICL and OCL in FIGS. 3 and 5, such that an upper half of the foot portion 12 substantially defines the instep area 14 while the lower half substantially defines the sole area 15. The upper instep area 14 has a front ankle region 21, an intermediate instep region 22, and a forward instep region 23. These regions 21, 22, 23 are axially divided by notional center line TCL in FIG. 6. The lower sole area 15 has inner and outer arch regions 25, 26 axially divided by center line BCL in FIG. 4, and a forward ball region 27 adjacent the toe 17. The inner arch region 25 is designed to reside substantially adjacent an inner arch of the wearer's foot, as best shown in FIG. 2, and incorporates a generally semi-circular, anatomically-shaped targeted compression zone 30 comprising elastic yarns, pattern (or accent) yarns, and axially extending compression ridges 32, discussed further below. When applied to the foot, the compression zone 30 of sock 10 may exert an intensified targeted compression force at the inner arch of the foot which is substantially greater than the compression force applied in other directly adjacent areas of the foot portion 12. The intensified compression may be as much as 3-4 times greater (or more) in the compression zone 30 of the sock 10.

Figure 3:
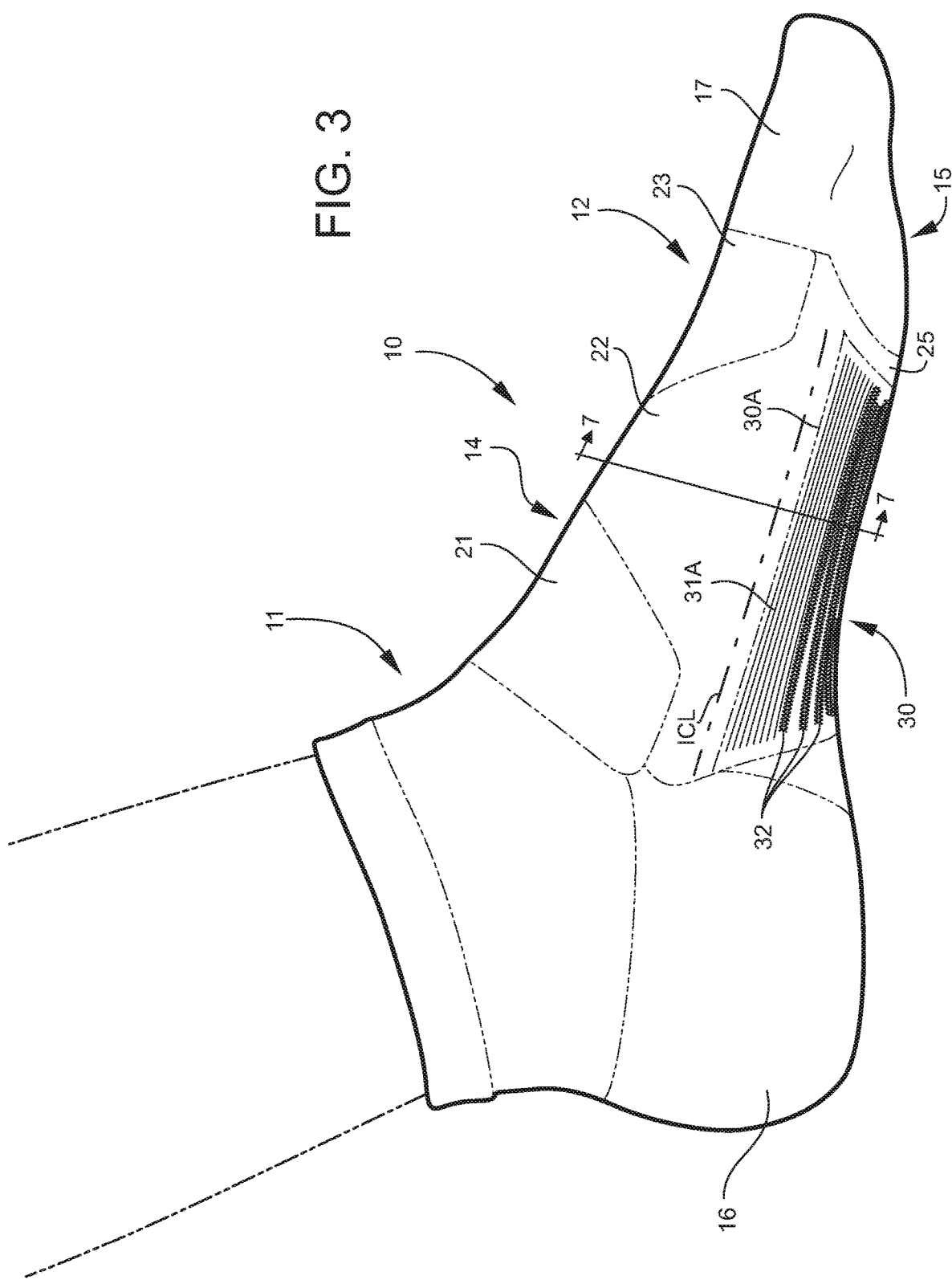
FIG. 3 is an inner arch side view of the exemplary sock.
Figure 4:
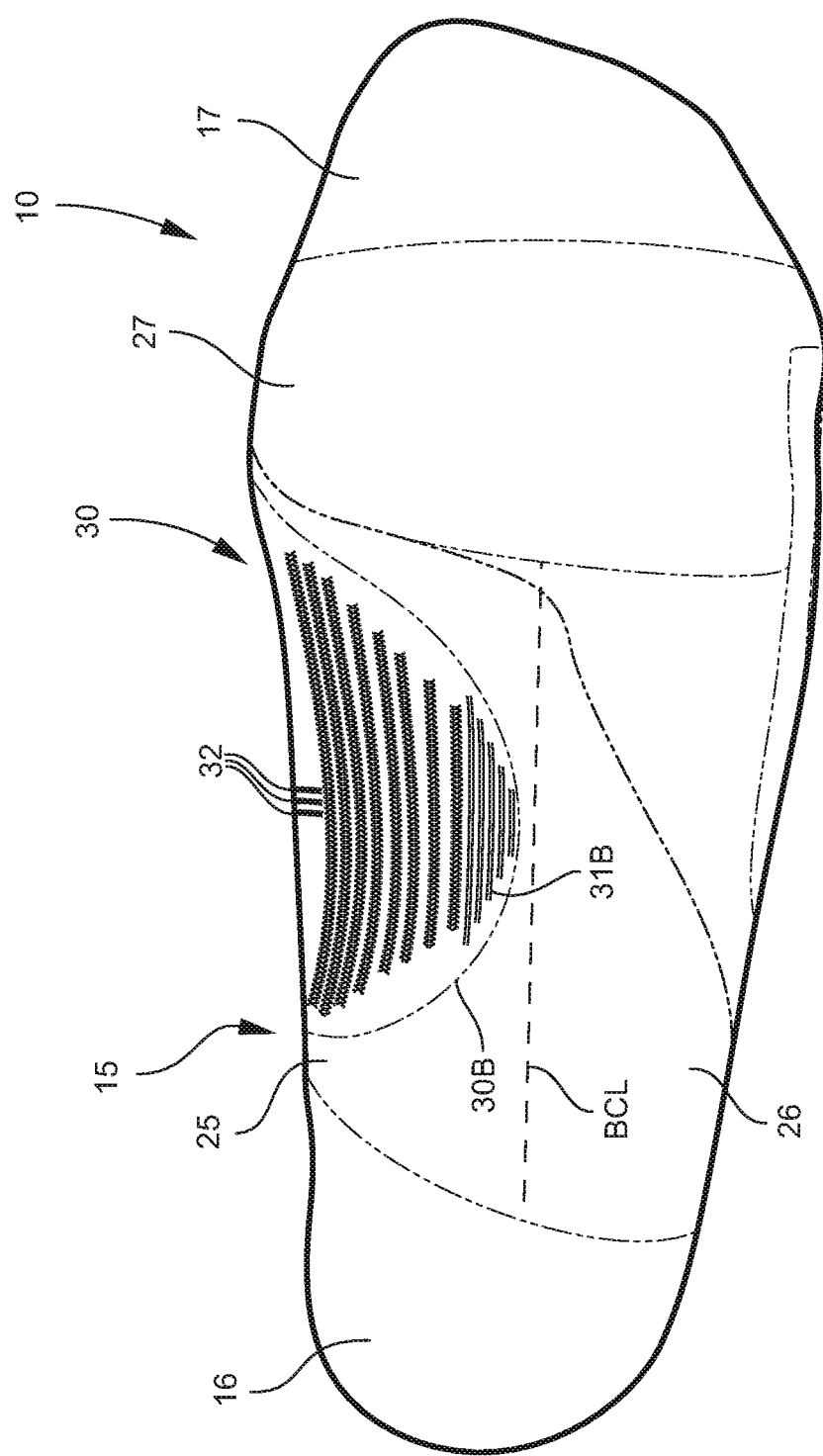
FIG. 4 is a bottom view of the exemplary sock.
Figure 5:
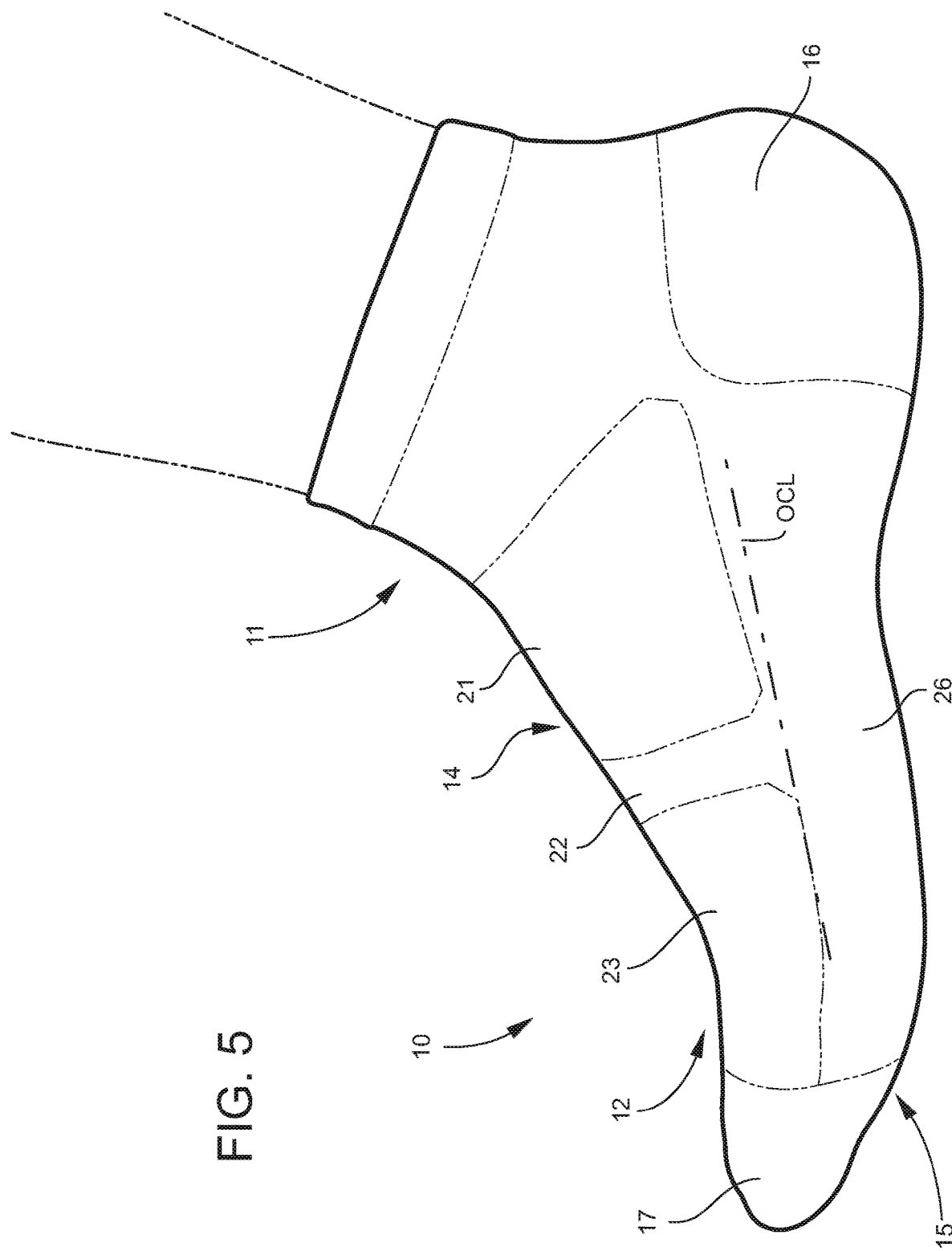
FIG. 5 is an outer arch side view of the exemplary sock.
Figure 6:
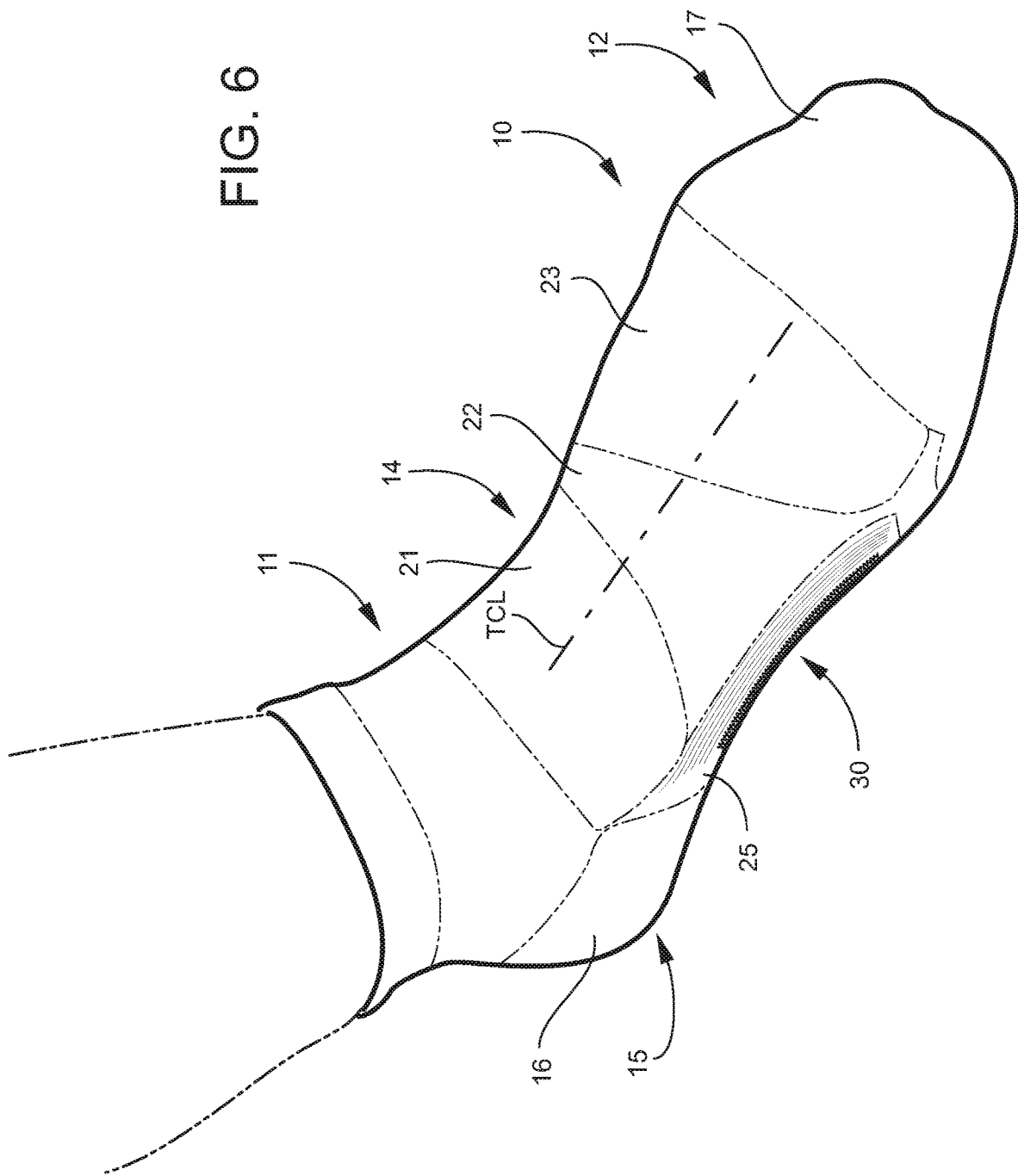
FIG. 6 is a top perspective view of the exemplary sock.
Figure 7:
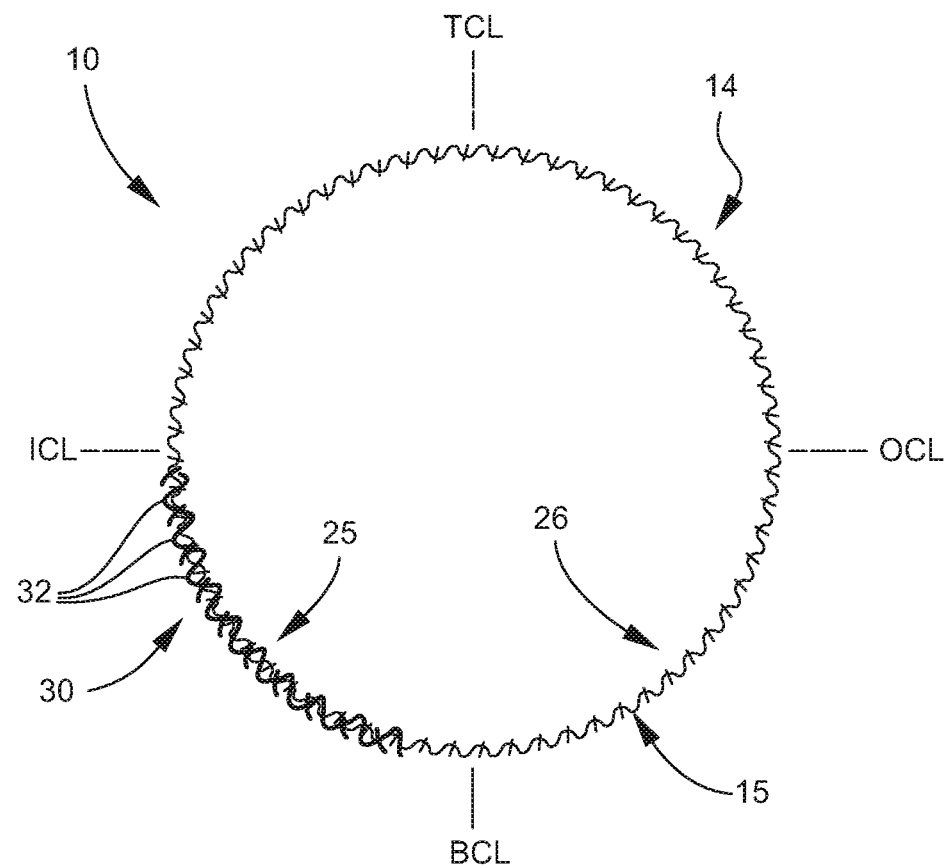
FIG. 7 is a cross-sectional view of the exemplary sock taken generally along line 7-7 of FIG. 3.

As best shown in FIGS. 3 and 4, the compression zone 30 has a substantially linear side 30A at its top margin 31A which extends adjacent the inside axial center line ICL of foot portion 12, and a substantially arcuate side 30B opposite the linear side 30A at its bottom margin 31B, and facing the bottom axial centerline BCL of the foot portion 12. FIG. 7 further illustrates quadrants of the circularly-knit foot portion 12 of sock 10. The quadrants are divided by respective center lines ICL, OCL, TCL, BCL discussed above. As shown, the targeted compression zone 30 may reside substantially entirely within the lower inside quadrant of the foot portion at the inner arch region 25 (substantially between ICL and BCL). The compression ridges 32 are spaced apart circumferentially from a top of the compression zone 30 to the bottom of the compression zone 30, and taper in axial length within a generally semi-circular shape between top and bottom margins 31A, 31B.

The remainder of the lower sole area 15 immediately surrounding the targeted compression zone 30 (both axially and circumferentially) comprises a less dense flat knit fabric structure with a one-by-one mock rib. The upper instep area 14 of the sock 10 may comprise a 1×1 mesh knit construction in the divided front ankle and forward instep regions 21, 23. The intermediate instep region 22 may incorporate a 1×1 mock rib construction similar to the fabric area immediately surrounding the compression zone 30. The heel and toe 16, 17 are formed in a conventional manner, and may also comprise mock ribbing. The ankle portion 11 of sock 10 may comprise a mesh knit elastic cuff, and mock ribbing knit in a conventional manner.

Exemplary Knit Structure of Compression Zone 30

Figure 8:
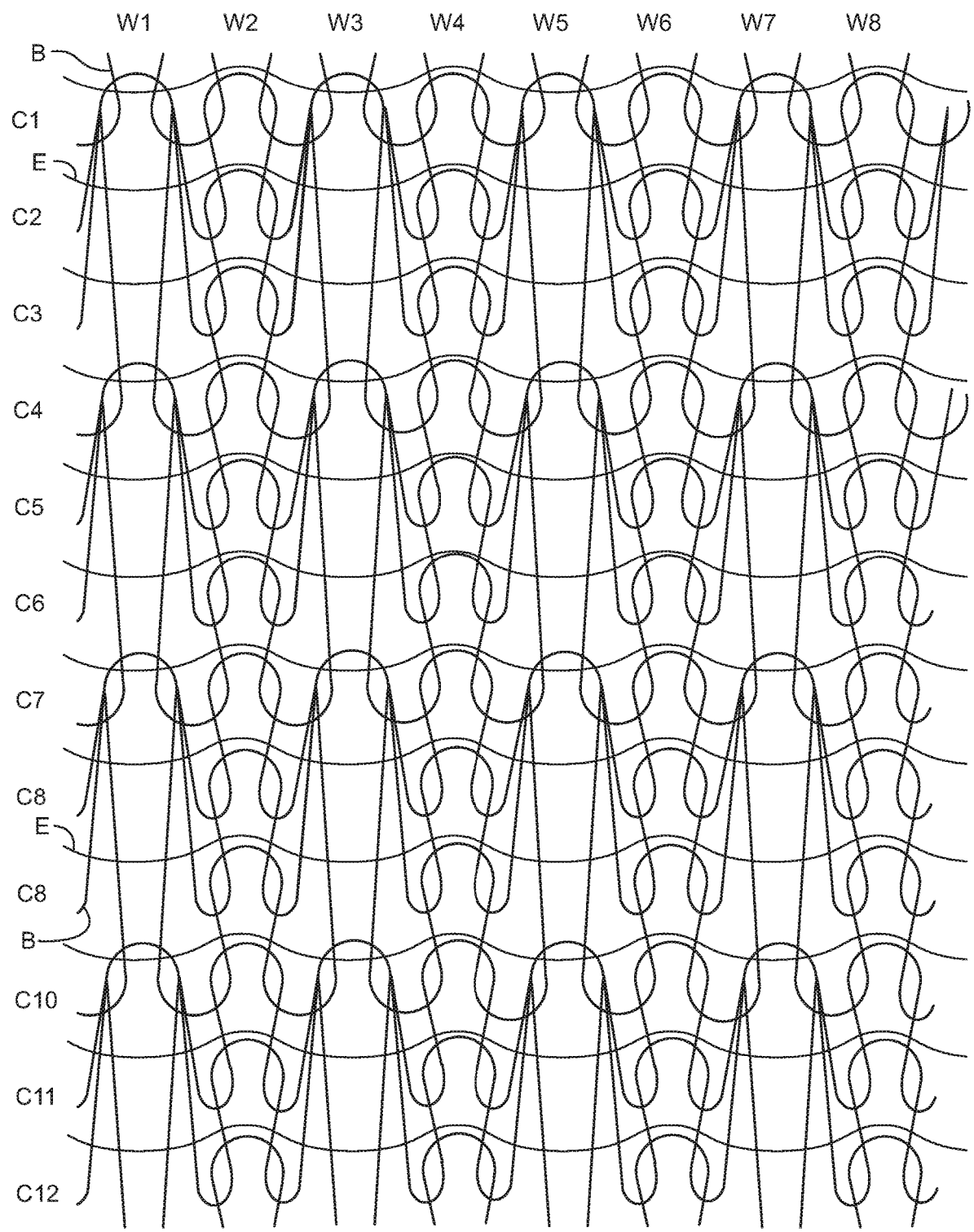
FIG. 8 illustrates an exemplary knit structure of top and bottom margins of the targeted compression zone.
Figure 9:
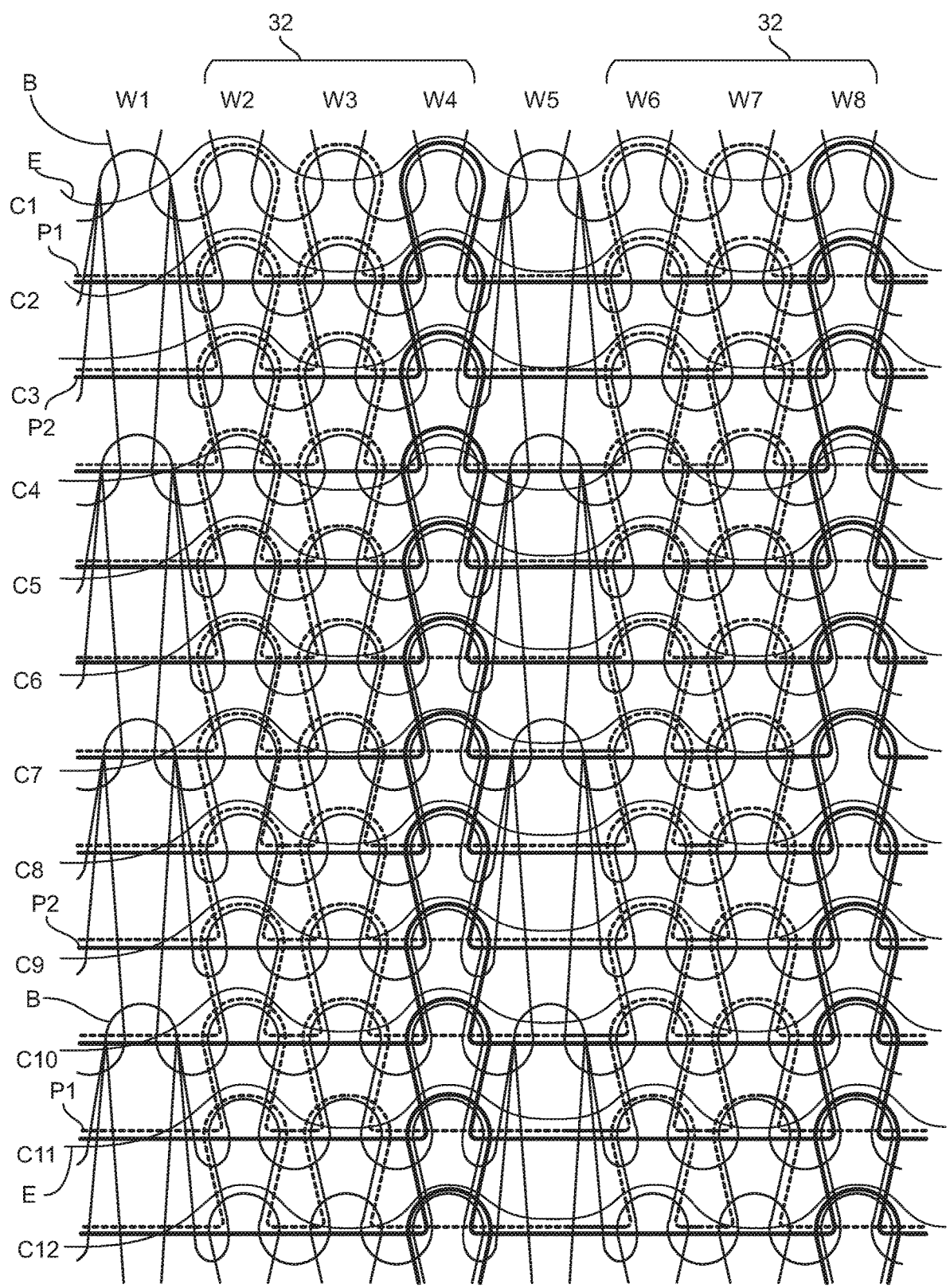
FIG. 9 illustrates an exemplary knit structure of the targeted compression zone between the top and bottom margins.

Referring to FIGS. 3, 4, 8, and 9, in the exemplary embodiment the targeted compression zone 30 of sock 10 is formed of a one-by-one mock rib construction with the elastic yarn (E) laid-in the plaited body yarn (B) on a reverse side of the fabric in each course C1-C12 by tuck and float stitches in needle loops of wales W1-W8. FIG. 8 illustrates the knit structure of the compression zone 30 in spaced top and bottom margins 31A, 31B—the compression zone 30, margins 31A, 31B, and axial compression ridges 32 being shown FIGS. 3 and 4. The axial compression ridges 32 between the margins 31A, 31B are formed by the introduction of two pattern yarns (P1) and (P2), shown in FIG. 9, integrally knit with the plaited body yarn (B) in each course C1-C12 in a manner using tuck and float stitches, such that the compression ridges 32 (W2-W4 and W6-W8) are raised and substantially more dense as compared to directly adjacent areas of the foot portion 12. For clarity of illustration, the pattern yarns (P1) and (P2) are distinguished in FIG. 9 by broken-lines and bold lines, respectively. In the exemplary embodiment, pattern yarn (P1) is knit in wales W2, W3, W6, and W7 of the plaited body yarn (B), and floats uncut across wales W1, W4, W5, and W8. Pattern yarn (P2) is knit in wales W4 and W8 of the plaited body yarn (B), and floats uncut across wales W1, W2, W3, W5, W6 and W7. As indicated previously, the compression zone 30 may be knit in a manner resulting in increased stitch density, tighter gauge, and reduced stretchability compared to directly adjacent areas of the foot portion 12.

Exemplary Sock 100

A further exemplary embodiment of the present disclosure is illustrated in FIGS. 10-14. The exemplary sock 100 incorporates the same knit structure described above in sock 10—providing targeted increased compression to the medial arch of the foot, as indicated at zone 30'. Compression zone 30' is generally semi-circular and anatomically-shaped, and comprises elastic yarns, pattern (or accent) yarns, and axially extending compression ridges 32' discussed further below. The present sock 100 utilizes this same knit structure to provide additional targeted and increased compression above and below the heel of the foot in the areas ("targeted compression zones") designated at 101 and 102, respectively. All other regions of the exemplary sock 100 may be constructed as described above in sock 10. The targeted compression is located in areas 101, 102 to lift and stretch the plantar fascia tissue on the bottom of the foot (originating in the heel), and to add compressive support to the Achilles tendon above the heel.

Like sock 10, the exemplary sock 100 is constructed on a circular hosiery knitting machine, and includes a plurality of yarns formed in needle and sinker loops extending in circumferential courses and axial wales. The sock 100 may be formed throughout of a body yarn and a ground yarn knitted in plated relationship in various stitch constructions described herein, and with inlaid elastic yarns and pattern yarns in certain portions, areas, and regions of the sock 100. The exemplary sock 100 comprises an integrally-knit raised ankle portion 110 and foot portion 112. The foot portion 112 incorporates same the sock structure described above, including a reciprocally-knitted heel 114 and closed toe 115. The ankle portion 110 defines an open leg end 116 of the sock 100.

The targeted compression zone 101 is formed with the foot portion 112 of the sock 100 between the heel 114 and the toe 115, and is adapted to extend under the foot of the wearer (adjacent the plantar fascia) generally from a lateral malleolus to a medial malleolus. Target compression zone 101 incorporates spaced-apart axial compression ridges 32' constructed in the manner previously described above (as compression ridges 32 in sock 10). The compression ridges 32' extend axially outward from the heel 114 at a first end of the compression zone 101 to a second end of the compression zone 101. In one embodiment, the heel 114 of the foot portion 112 comprises a heel pocket defined by lower and upper reciprocation lines 121 and 122. The first end of the targeted compression zone 101 is formed at the lower reciprocation line 121 of the heel 114, and extends axially from the heel 114 in a direction towards the toe 115 of the sock 100. The second end of the targeted compression zone 101 is centrally pointed, such that adjacent compression ridges 32' have different termination points along the foot portion 112—the compression ridges 32' being shortest at opposite ends of the zone 101 (proximate the maleolae) and progressively increasing in length to the longest center ridge 32'.

The targeted compression zone 102 is formed with the ankle portion 110 of the sock 100 between the heel 114 and the open leg end 116, and is adapted to extend around a back of the wear's heel (adjacent the Achilles tendon) generally from the lateral malleolus to the medial malleolus. Like targeted compression zone 101, compression zone 102 incorporates spaced-apart axial compression ridges 32' constructed in the manner previously described above. The compression ridges 32' extend axially outward from the heel 114 at a first end of the compression zone 102 to a second end of the compression zone 102. The first end of the targeted compression zone 102 is formed at the upper reciprocation line 122 of the heel pocket, and extends axially from the heel 114 in a direction towards the open leg end 116 of the sock 100. The second end of the targeted compression zone 102 is centrally pointed, such that adjacent compression ridges 32' have different termination points along the raised ankle portion 110. The compression ridges 32' are shortest at opposite ends of the zone 102 (proximate the maleolae), and progressively increase in length to the longest center ridge 32' extending axially upward from the heel 114.

When sock 100 is properly applied to the foot, the targeted compression zones 30', 101, and 102 exert an intensified targeted compression force at the inner arch of the foot, the plantar fascia tissue (originating in the heel), and the Achilles tendon above the heel. This targeted compression is substantially greater than the compression force applied in other directly adjacent areas of the sock 100. The intensified compression may be as much as 3-4 times greater (or more) in the compression zones 30', 101, and 102 of the sock 10. The remainder of the sock 100 immediately surrounding the targeted compression zones 30', 101, and 102 (both axially and circumferentially) may comprise a less dense flat or mesh knit fabric structure with a one-by-one mock rib. The heel and toe 114, 115 of the sock 100 may be formed in a conventional manner, as described above, and may also comprise mock ribbing. The ankle portion 110 of sock 100 may comprise a mesh knit elastic cuff, and mock ribbing knit in a conventional manner.

Figure 10:
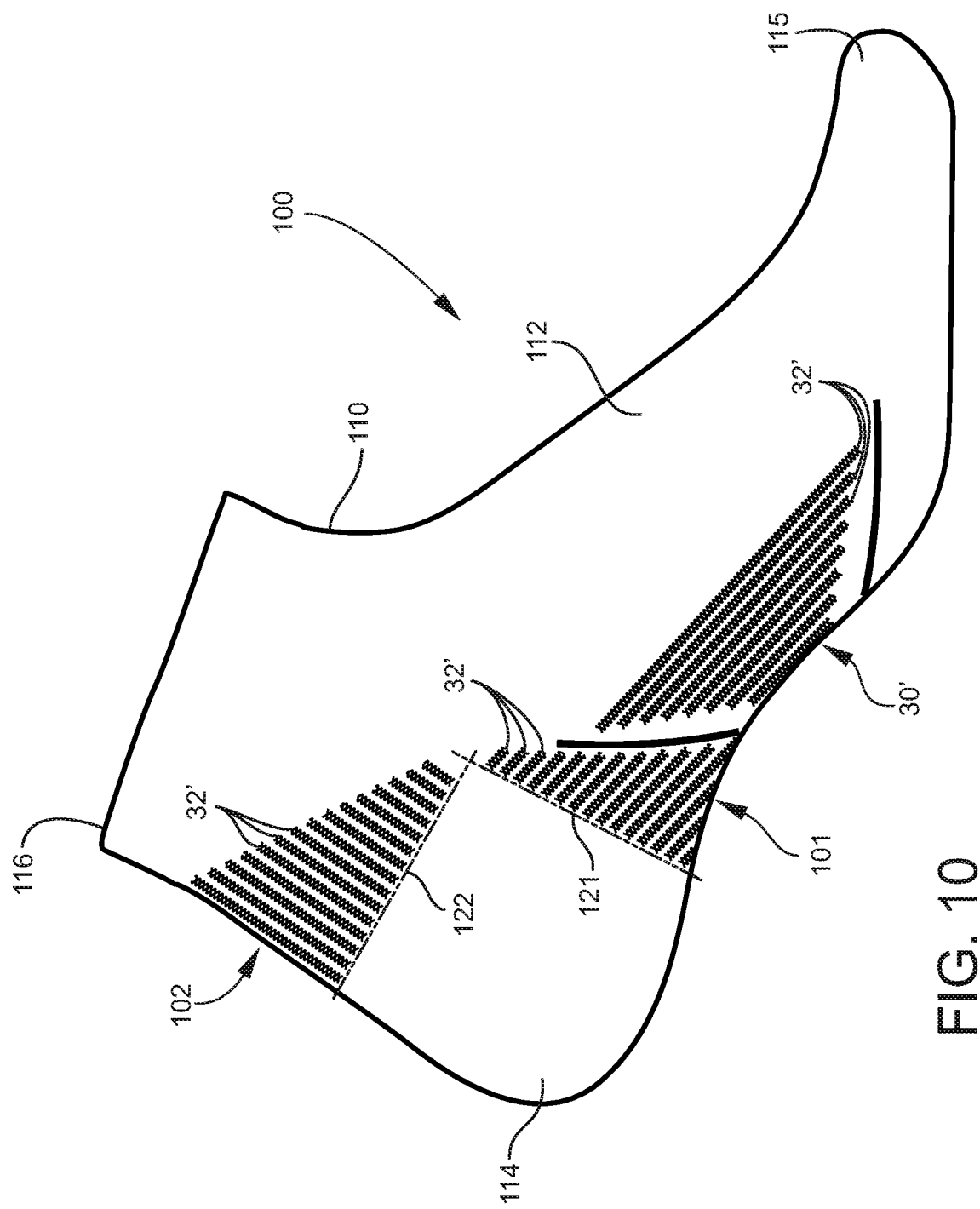
FIGS. 10-13 illustrate a further exemplary embodiment of a knit sock according to the present disclosure.
Figure 11:
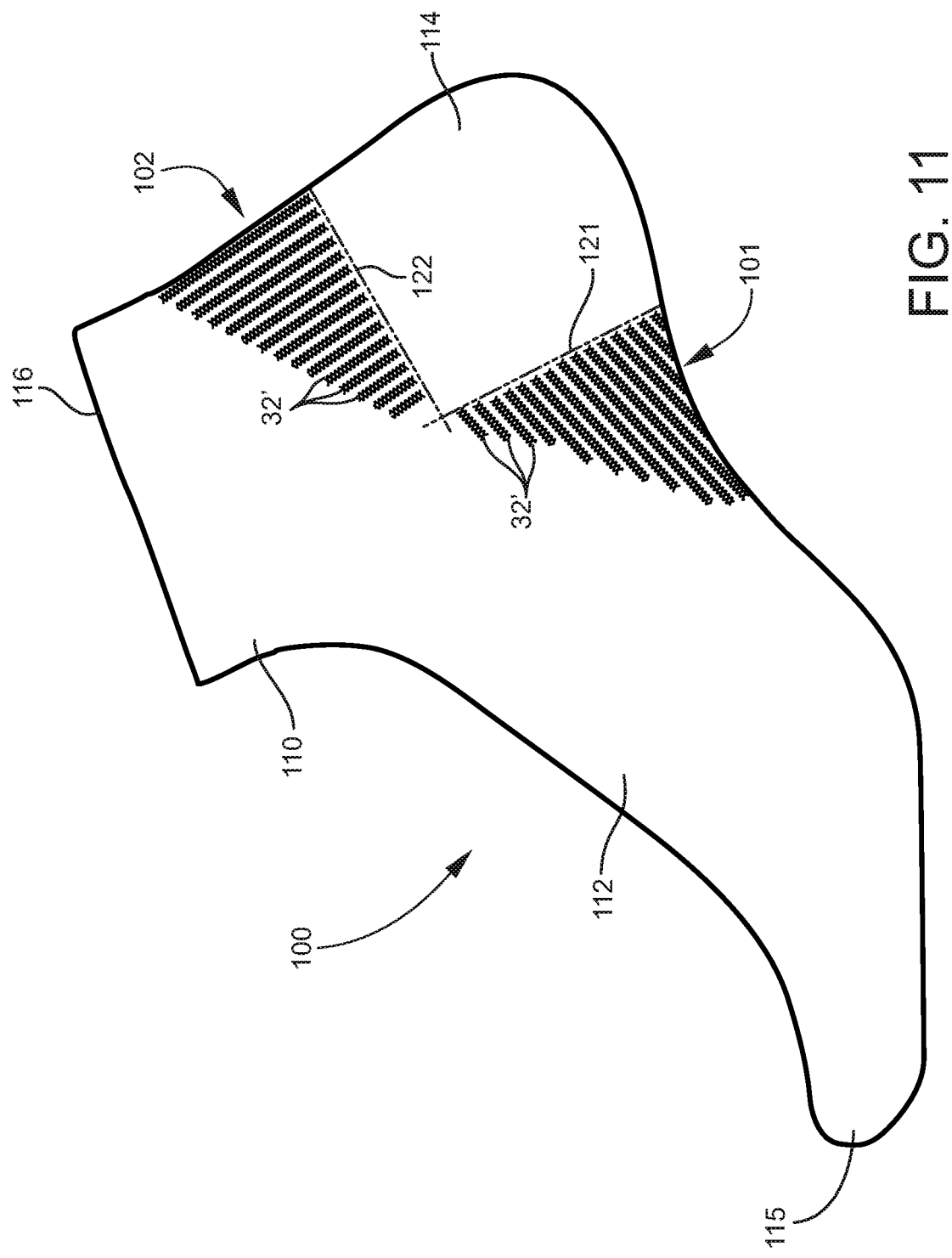
Figure 12:
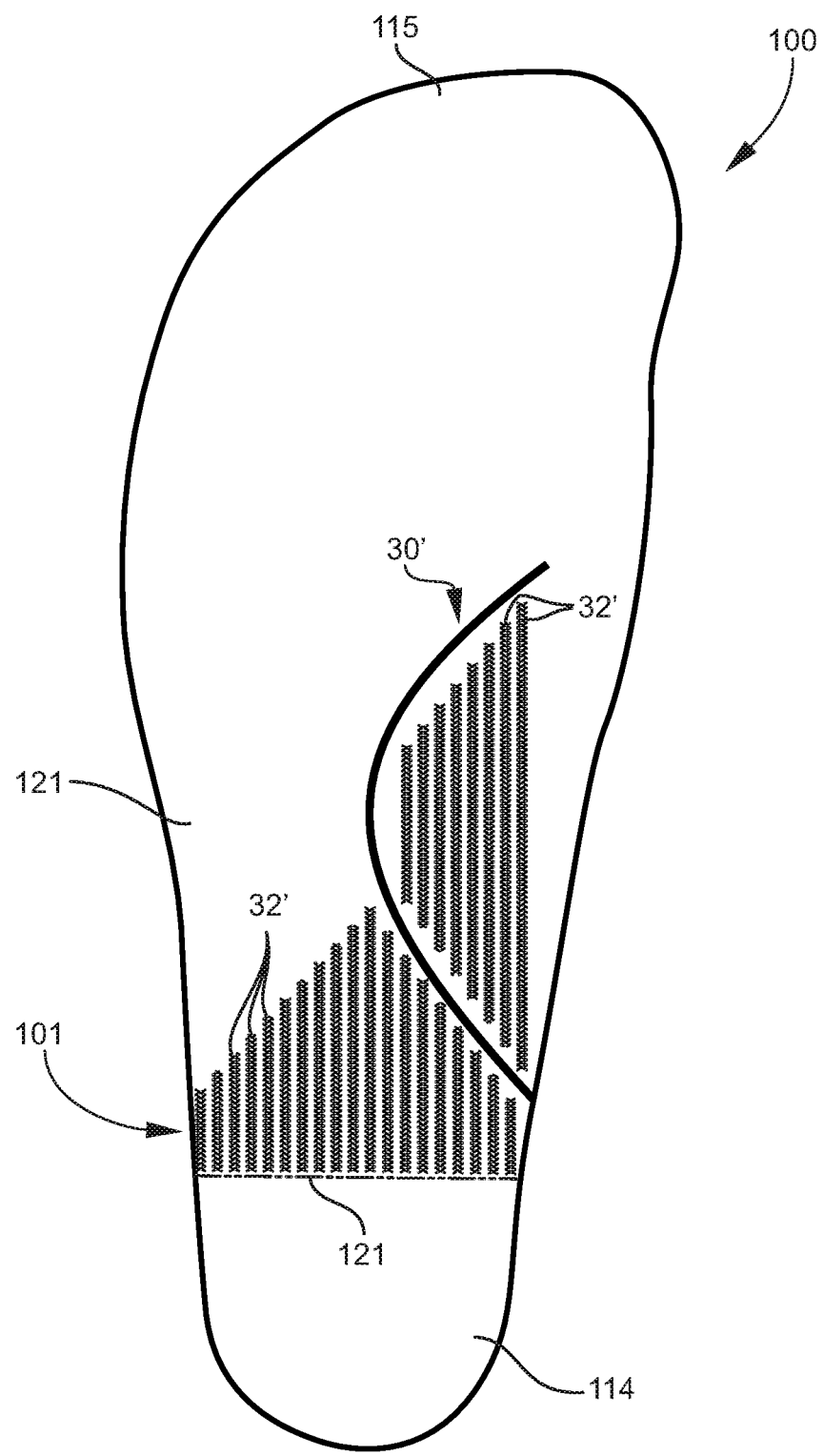
Figure 13:
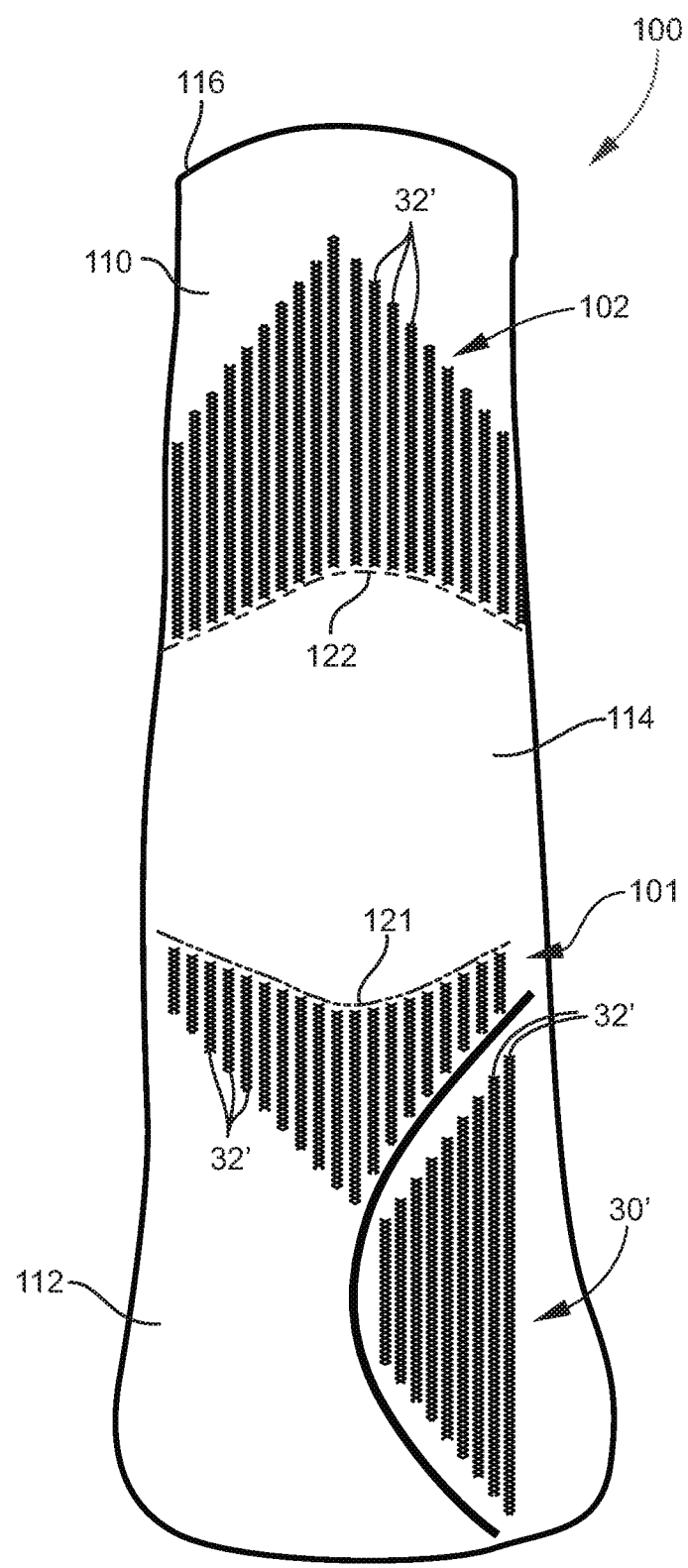
Figure 14:
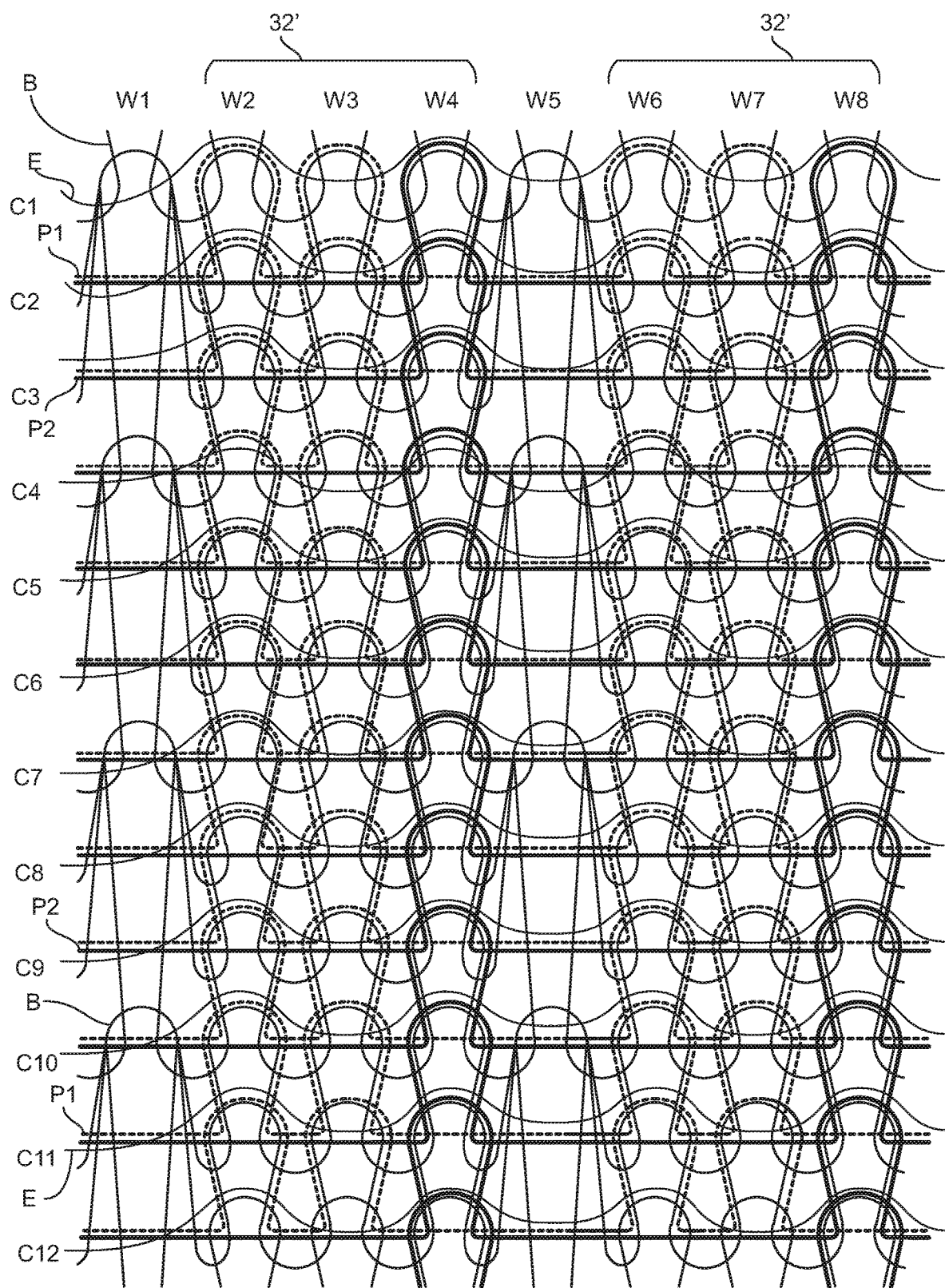
FIG. 14 illustrates an exemplary knit structure of the targeted compression zones in the sock shown in FIGS. 10-13.

Referring to FIGS. 10, 13 and 14, in the exemplary embodiment the targeted compression zones 30', 101 and 102 of sock 100 may be constructed in a manner similar to that of compression zone 30 in sock 10. For example, compression zones 30', 101, and 102 may be formed of a one-by-one mock rib construction with the elastic yarn (E) laid-in the plaited body yarn (B) on a reverse side of the fabric in each course C1-C12 by tuck and float stitches in needle loops of wales W1-W8. The courses and wales shown in FIG. 14 are numbered for reference purposes only and are not intended to designate any specific course or wale in sock 100. The exemplary compression ridges 32' are formed by the introduction of two pattern yarns (P1) and (P2), shown in FIG. 14, integrally knit with the plaited body yarn (B) in each course C1-C12 in a manner using tuck and float stitches, such that the compression ridges 32' (W2-W4 and W6-W8) are raised and substantially more dense as compared to directly adjacent areas of the sock 100. For clarity of illustration, the pattern yarns (P1) and (P2) are distinguished in FIG. 14 by broken-lines and bold lines, respectively. In the exemplary embodiment, pattern yarn (P1) is knit in wales W2, W3, W6, and W7 of the plaited body yarn (B), and floats uncut across wales W1, W4, W5, and W8. Pattern yarn (P2) is knit in wales W4 and W8 of the plaited body yarn (B), and floats uncut across wales W1, W2, W3, W5, W6 and W7. As indicated previously, the compression zones 30', 101 and 102 may be knit in a manner resulting in increased stitch density, tighter gauge, and reduced stretchability compared to directly adjacent areas of the sock 100.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112(f) [or 6th paragraph/pre-AIA] is not intended. Additionally, it is not intended that the scope of patent protection afforded the present invention be defined by reading into any claim a limitation found herein that does not explicitly appear in the claim itself.

What is claimed:

1. A knit sock integrally formed of a body yarn in circumferential courses and axial wales, said sock comprising:
   a foot portion having a heel and a toe;
   an ankle portion joined to said foot portion and defining an open leg end of said sock;
   a first targeted compression zone formed with said foot portion between the heel and the toe, and comprising spaced-apart axial compression ridges extending axially outward from the heel at a first end of said first compression zone to a second end of said first compression zone, and wherein said axial compression ridges have different coursewise termination points at the second end of said first compression zone;
   a second targeted compression zone formed with said ankle portion between the heel and the open leg end of said sock, and comprising spaced-apart axial compression ridges extending axially outward from the heel at a first end of said second compression zone to a second end of said second compression zone, and wherein said axial compression ridges have different coursewise termination points at the second end of said second compression zone; and
   whereby a compression force applied by said sock within said first and second targeted compression zones is greater than the compression force in directly adjacent areas of said sock.

2. The knit sock according to claim 1, wherein said first and second targeted compression zones comprise elastic yarns laid-in the body yarn.

3. The knit sock according to claim 1, wherein said axial compression ridges comprise individual uncut pattern yarns integrally formed with respective courses of the body yarn within said first and second targeted compression zones.

4. The knit sock according to claim 1, wherein said first targeted compression zone is centrally pointed at its second end, and is adapted to extend under the foot generally from a lateral malleolus to a medial malleolus of the wearer.

5. The knit sock according to claim 1, wherein said second targeted compression zone is centrally pointed at its second end, and is adapted to extend around a back of the heel generally from a lateral malleolus to a medial malleolus of the wearer.

6. The knit sock according to claim 1, wherein the heel of said foot portion comprises a heel pocket defined by upper and lower reciprocation lines, and wherein the first end of said first targeted compression zone is formed at the lower reciprocation line of said heel pocket, and extends axially from said heel pocket towards the toe of said foot portion.

7. The knit sock according to claim 1, wherein the heel of said foot portion comprises a heel pocket defined by upper and lower reciprocation lines, and wherein the first end of said second targeted compression zone is formed at the upper reciprocation line of said heel pocket, and extends axially from said heel pocket towards the open leg end of said sock.

8. The knit sock according to claim 1, wherein said first and second targeted compression zones comprise double covered elastic yarns.

9. The knit sock according to claim 8, wherein said double covered elastic yarns are greater than 250 denier.

10. The knit sock according to claim 1, wherein said first and second targeted compression zones have an increased density as compared to directly adjacent areas of said sock.

11. The knit sock according to claim 1, wherein said first and second targeted compression zones have a knit structure distinct from directly adjacent areas of said sock.

12. A knit sock integrally formed of a body yarn in circumferential courses and axial wales, said sock comprising:
   a foot portion having a heel and a toe;
   an ankle portion joined to the foot portion and defining an open leg end of said sock;
   a targeted compression zone formed with said ankle portion between the heel and the open leg end of said sock, and comprising spaced-apart axial compression ridges extending axially outward from the heel at a first end of said targeted compression zone to a second end of said targeted compression zone, and wherein said axial compression ridges have different coursewise termination points at the second end of said targeted compression zone; and whereby a compression force applied by said sock within said targeted compression zone is greater than the compression force in directly adjacent areas of said sock.

13. The knit sock according to claim 12, wherein said targeted compression zone comprises elastic yarns laid-in the body yarn.

14. The knit sock according to claim 12, wherein said axial compression ridges comprise individual uncut pattern yarns integrally formed with respective courses of the body yarn within said targeted compression zone.

15. The knit sock according to claim 12, wherein said targeted compression zone is centrally pointed at its second end, and is adapted to extend around a back of the heel generally from a lateral malleolus to a medial malleolus of the wearer.

16. The knit sock according to claim 12, wherein the heel of said foot portion comprises a heel pocket defined by upper and lower reciprocation lines, and wherein the first end of said targeted compression zone is formed at the upper reciprocation line of said heel pocket, and extends axially from the heel pocket towards the open leg end of said sock.

17. The knit sock according to claim 12, wherein said targeted compression zone comprises double covered elastic yarns.

18. The knit sock according to claim 17, wherein said double covered elastic yarns are greater than 250 denier.

19. The knit sock according to claim 12, wherein said targeted compression zone has an increased density as compared to directly adjacent areas of said sock.

20. The knit sock according to claim 12, wherein said targeted compression zone has a knit structure distinct from directly adjacent areas of said sock.

* * * * *